United States Patent [19]

Sano et al.

[11] 4,006,057

[45] Feb. 1, 1977

[54] METHOD OF PRODUCING L-CYSTEINE AND L-CYSTINE

[75] Inventors: Konosuke Sano, Machido; Keizo Matsuda, Kawasaki; Koji Mitsugi, Yokohama; Kazuhiko Yamada, Fujisawa; Fumihide Tamura, Kawasaki; Naohiko Yasuda, Yokosuka; Ichiro Noda, Yokohama, all of Japan

[73] Assignee: Ajinomoto Co., Inc., Tokyo, Japan

[22] Filed: Nov. 4, 1975

[21] Appl. No.: 628,840

[30] Foreign Application Priority Data

Nov. 6, 1974 Japan .......................... 49-127153
Dec. 3, 1974 Japan .......................... 49-137697

[52] U.S. Cl. .................................. 195/29; 195/30
[51] Int. Cl.² ....................................... C12D 13/06
[58] Field of Search ...................... 195/28, 29, 30

[56] References Cited

OTHER PUBLICATIONS

Chemical Abstracts, vol. 57, 7727d, 1962.

*Primary Examiner*—A. Louis Monacell
*Assistant Examiner*—Robert J. Warden
*Attorney, Agent, or Firm*—Oblon, Fisher, Spivak, McClelland & Maier

[57] ABSTRACT

A method for producing L-cysteine and/or L-cystine which comprises:

a. holding 2-amino-thiazoline-4-carboxylic acid in an aqueous solution at a pH of 5 to 11 in the presence of an effective amount of enzyme produced by a microorganism; said enzyme being capable of converting the 2-amino-thiazoline-4-carboxylic acid to L-cysteine and/or L-cystine, and said microorganism being capable of growing in a medium containing 2-amino-thiazoline-4-carboxylic acid as a nitrogen source; and b. recovering the L-cysteine and/or L-cystine formed from said aqueous solution.

17 Claims, No Drawings

METHOD OF PRODUCING L-CYSTEINE AND L-CYSTINE

This invention relates to a method for producing L-cysteine and L-cystine.

Hitherto, L-cystine has been isolated from hydrolyzates of protein-rich materials such as hair. And L-cysteine has been produced by reducing L-cystine. However, hair is not available stably in lower price.

Therefore, it is the object of this invention to provide a process for producing L-cysteine and L-cystine commercially at a lower cost.

It has now been found that 2-amino-thiazoline-4-carboxylic acid (hereinafter referred to as ATC), which is available in a large quantity and at a lower cost than hair, is enzymatically converted in a very high yield to L-cysteine and L-cystine. It has further been found that the enzyme having the activity of converting ATC to L-cysteine and L-cystine (hereinafter referred to as ATC hydrolyzing enzyme) is produced by various microorganisms, especially bacteria. The microorganism which produces ATC hydrolyzing enzyme can be selected as a grower in a medium containing ATC as a nitrogen source.

This invention is explained more particularly below:

The microorganisms which produce the ATC hydrolyzing enzyme are widely distributed especially in bacteria. The microorganisms can grow in a medium containing ATC as the sole nitrogen source and are easily obtained by the following method from natural sources:

Samples from a natural source containing microorganisms are inoculated on the screening medium which contains, per deciliter, 0.3 g DL-ATC·3H$_2$O, 1.0 g glycerol, 0.01 g yeast extract, 0.1 g KH$_2$PO$_4$, 0.05 g MgSO$_4$·7H$_2$O, and 2.0 g agar, and of pH 7.0. The inoculated medium is incubated at 30° C for 1 to 5 days.

Almost all the microorganisms which grow on the medium mentioned above produce the ATC hydrolyzing enzyme.

Production of L-cysteine and/or L-cystine from ATC by the microorganism grown on the screening medium can be confirmed by holding with the enzyme of the microorganism a reaction mixture containing per deciliter, 1.0 g DL-ATC·3H$_2$O, 0.01 g pyridoxalphosphate and 1.0 g KH$_2$PO$_4$, of pH 8, for 24 hours at 30° C. L-Cysteine and L-cystine produced in the reaction mixture are detectable by paper-chromatography.

Specimen cultures capable of producing the enzyme are as follows:

| | | |
|---|---|---|
| Sarcina lutea | AJ 1217 | ATCC 272 |
| Achromobacter delmarvae | AJ 1983 | FERM-P 21 |
| Alcaligenes denitrificans | AJ 2553 | ATCC 15173 |
| Bacillus brevis | AJ 1282 | ATCC 8185 |
| Brevibacterium flavum | AJ 1516 | ATCC 13826 |
| Enterobacter aerogenes | AJ 2643 | FERM-P 2764 |
| Erwinia carotovora | AJ 2753 | FERM-P 2766 |
| Escherichia coli | AJ 2592 | FERM-P 2763 |
| Micrococcus sodonensis | AJ 1753 | ATCC 11880 |
| Mycoplana dimorpha | AJ 2809 | ATCC 4279 |
| Serratia marcescens | AJ 2698 | FERM-P 2765 |
| Flavobacterium acidoficum | AJ 2494 | ATCC 8366 |
| Pseudomonas ovalis | AJ 2236 | FERM-P 2762 |
| Pseudomonas thiazolinophilum | AJ 3854 | FERM-P 2810 |
| Pseudomonas ovalis | AJ 3863 | FERM-P 2811 |
| Pseudomonas desmolytica | AJ 3868 | FERM-P 2816 |
| Pseudomonas desmolytica | AJ 3869 | FERM-P 2817 |
| Pseudomonas cohaerens | AJ 3874 | FERM-P 2831 |
| Pseudomonas ovalis | AJ 3864 | FERM-P 2812 |
| Pseudomonas ovalis | AJ 3865 | FERM-P 2813 |
| Pseudomonas ovalis | AJ 3866 | FERM-P 2814 |
| Pseudomonas ovalis | AJ 3867 | FERM-P 2815 |
| Pseudomonas desmolytica | AJ 3870 | FERM-P 2818 |
| Pseudomonas desmolytica | AJ 3871 | FERM-P 2819 |
| Pseudomonas desmolytica | AJ 3872 | FERM-P 2820 |
| Pseudomonas desmolytica | AJ 3873 | FERM-P 2821 |

AJ 3854, AJ 3863, AJ 3868, AJ 3869, AJ 3874, AJ 3865, AJ 3871, AJ 3870, AJ 3864, AJ 3866, AJ 3867, AJ 3873 and AJ 3872 are newly isolated by the inventors.

Taxonomic characteristics of the newly isolated strains are as follows:

| | AJ 3854 | AJ 3863 | AJ 3868 | AJ 3869 | AJ 3874 |
|---|---|---|---|---|---|
| Cell form | rods 0.6–0.8 × 1.5–2$\mu$ | rods 0.6–0.8 × 1.3–1.8$\mu$ | rods 0.6–0.8 × 1.4–1.8$\mu$ | rods 0.6–0.8 × 1.4–1.8$\mu$ | rods 0.6–0.8 × 1.2–2$\mu$ |
| Pleomorphism | none | none | none | none | none |
| Motility | motile | motile | motile | motile | motile |
| Flagellation | polar | polar | polar | polar | polar |
| Spore | absent | absent | absent | absent | absent |
| Acid fast | negative | negative | negative | negative | negative |
| Gram stain | | | | | |
| 12 hrs | negative | negative | negative | negative | negative |
| 24 | negative | negative | negative | negative | negative |
| 72 | negative | negative | negative | negative | negative |
| Agar colonies | | | | | |
| growth | moderate | abundant | moderate | moderate | abundant |
| form | circular | circular | circular | circular | circular |
| elevation | convex | convex | convex | convex | convex |
| edge | entire | entire | entire | entire | entire |
| color | buff | rosy buff | straw | buff-rosy buff | pale luteous |
| Agar slant | | | | | |
| growth | good | abundant | abundant | abundant | abundant |
| surface | smooth | smooth rosy | smooth | smooth rosy | smooth pale |
| color | buff | buff | straw | buff | luteous |
| luster | translucent | translucent | translucent | opaque | translucent |
| form | filiform | filiform | filiform | filiform | filiform |

-continued

| | AJ 3854 | AJ 3863 | AJ 3868 | AJ 3869 | AJ 3874 |
|---|---|---|---|---|---|
| Nutrient broth | | | | | |
| turbidity | turbid | turbid | turbid | turbid | turbid |
| growth on surface | none | none | ring | none | none |
| sedimentation | sediment | sediment | sediment | sediment | sediment |
| Gelatin stab | | | | | |
| 20° C (1 month) | − | − | − | − | ++ |
| 37° C (1 month) | − | − | − | − | +++ |
| Gelatin plate | | | | | |
| growth | + | + | + | + | ++ |
| liquefaction | − | − | − | − | ++ |
| Growth on King's medium B | ++ | +++ | +++ | +++ | +++ |
| water soluble pigment | none | yellowish-green fluorecent | none | none | none |
| Growth on glutamate-medium | ++ | ++ | ++ | ++ | ++ |
| Water soluble pigment | none | yellowish-green fluorecent | none | none | pale brown |
| Litmus milk | | | | | |
| reduction | not reduced | not reduced | not reduced | slightly reduced | not reduced |
| liquefaction | − | − | − | − | +++ |
| BCP milk | | | | | |
| pH | alkaline | alkaline | alkaline | alkaline | alkaline |
| liquefaction | − | − | − | − | +++ |
| Tyrosine-bouillon plate | | | | | |
| growth | ++ | ++ | +++ | +++ | +++ |
| water soluble pigment | − | − | − | − | − |
| Reduction of nitrates | | | | | |
| bouillon medium | ++ | +++ | ± | ± | ++ |
| synthetic medium | + | +++ | + | + | ++ |
| MR test | − | − | − | − | − |
| VP test | | | | | |
| pH (1 week) | 5.1 | 4.9 | 7.5 | 7.5 | NT |
| Indole | − | − | − | − | − |
| $H_2S$ | + | ± | ± | ± | ± |
| Hydrolysis of starch | − | − | − | − | − |
| Utilization of citric acid | | | | | |
| Koser's medium | + | + | + | ++ | ++ |
| Christensen's medium | ++ | +++ | +++ | +++ | +++ |
| Assimilation of inorganic nitrogen | | | | | |
| nitrate | +++ | +++ | + | − | +++ |
| ammonia | +++ | +++ | +++ | − | +++ |
| Water soluble pigment | none | Yellowish-green fluorecent | none | none | none |
| Catalase | − | − | − | − | − |
| Urease | − | ++ | ++ | ++ | ± |
| Oxidase | +++ | +++ | +++ | +++ | − |
| Growth pH | 5 − 9 | 5 − 9 | 5 − 9 | 5 − 9 | 6 − 9 |
| Maximum temp. of growth | 35° C | 39° C | 37° C | 38° C | 38° C |

-continued

| | AJ 3854 | AJ 3863 | AJ 3868 | AJ 3869 | AJ 3874 |
|---|---|---|---|---|---|
| Optimum temp. of growth | 20–35° C | 20–37° C | 25–37°C | 28–38° C | 37° C |
| Aerobiosis | aerobic | aerobic | aerobic | aerobic | aerobic |
| Formation of acid and gas from carbohydrates | acid gas | acid gas | acid gas | acid gas | acid gas |
| L-arabinose | – – | – – | – – | – – | + – |
| D-xylose | – – | +++ – | – – | – – | – – |
| D-glucose O | ++ – | ++ – | ++ – | ++ – | ++ – |
| F | – – | – – | – – | – – | – – |
| D-mannose | ++ – | +++ – | ++ – | +++ – | ± – |
| D-fructose | – – | ++ – | – – | – – | – – |
| D-galactose | ++ – | +++ – | – – | ++ – | – – |
| maltose | – – | – – | – – | – – | – – |
| saccharose | – – | – – | – – | – – | – – |
| lactose | – – | – – | – – | – – | +++ – |
| trehalose | – – | – – | – – | – – | – – |
| D-sorbitol | – – | – – | – – | – – | – – |
| D-mannitol | – – | – – | – – | – – | – – |
| inositol | – – | – – | – – | – – | – – |
| glycerine | – – | – – | – – | ++ – | – – |
| starch | – – | – – | – – | – – | – – |
| D-ribose | – – | +++ – | – – | – – | – – |
| L-rhamnose | – – | – – | – – | – – | – – |
| L-raffinose | – – | – – | – – | – – | – – |
| Formation of acid and gas from carbohydrates | acid gas | acid gas | acid gas | acid gas | acid gas |
| erithritol | – – | – – | – – | – – | – – |
| dulcitol | – – | – – | – – | – – | – – |
| cellobiose | – – | – – | – – | – – | – – |
| melibiose | ;31 – | +++ – | – – | – – | – – |
| adonitol | – – | – – | – – | – – | – – |
| salicin | – – | – – | – – | – – | – – |
| esculin | – – | – – | – – | – – | – – |
| Hydrolysis of casein | – | – | – | – | ++ |
| Hydrolysis of DNA | ++ | ++ | ++ | ++ | + |
| Growth on NaCl medium | no growth on 2 g/dl | growth on 5 g/dl | growth on less than 2 g/dl | growth on less than 2 g/dl | growth on 2 g/dl |
| Assimilation | | | | | |
| p-hydroxybenzoic acid | ++ | +++ | ++ | ++ | NT |
| gluconic acid | +++ | +++ | +++ | +++ | NT |
| lactose | – | – | – | – | NT |
| mannitol | + | + | – | + | NT |
| ammonium acetate | +++ | +++ | – | – | NT |
| lactic acid | +++ | +++ | +++ | ++ | +++ |
| glucose | ++ | ++ | ++ | ++ | NT |
| xylose | + | ++ | ++ | ++ | NT |
| protocatecuic acid | – | ++ | – | – | +++ |
| Desoxycholic acid medium made by "EIKEN" Co. growth (35° C 1 day) | – | ++ | ++ | + | + |
| GC content in DNA | 58.3% | NT | NT | NT | NT |
| Decomposition of riboflavin | – | NT | NT | NT | NT |
| Formation of indigotin from indol | – | NT | NT | NT | NT |

| | AJ 3865 | AJ 3871 | AJ 3870 | AJ 3864 | AJ 3866 | AJ 3867 | AJ 3873 | AJ 3872 |
|---|---|---|---|---|---|---|---|---|
| Cell form | rods | rods | rods | rods | rods | rods | rods | rods |
| Gram stain | negative | negative | negative | negative | negative | negative | negative | negative |
| Motility | motile | motile | motile | motile | motile | motile | motile | motile |

-continued

|  | AJ 3865 | AJ 3871 | AJ 3870 | AJ 3864 | AJ 3866 | AJ 3867 | AJ 3873 | AJ 3872 |
|---|---|---|---|---|---|---|---|---|
| Flagellation | polar | polar | polar | polar | polar | polar | polar | polar |
| Catalase | positive | positive | positive | positive | positive | positive | positive | positive |
| Oxydase | positve | positive | positive | positive | positive | positive | positive | positive |
| Aerobiosis | aerobic | aerobic | aerobic | aerobic | aerobic | aerobic | aerobic | aerobic |
| King's B-medium |  |  |  |  |  |  |  |  |
| growth | ++ yellowish-green | ++ | + | ± | ++ yellowish-green | ++ yellowish-green | + | + |
| water soluble pigment | fluorecent | none | none | none | fluorecent | fluorecent | none | none |
| Glutamic acid-medium |  |  |  |  |  |  |  |  |
| growth | +++ yellowish-green | +++ | +++ | +++ yellowish-green | +++ yellowish-green | +++ yellowish-green | ++ | ++ |
| water soluble pigment | fluorecent | none | none | fluorecent | fluorecent | fluorecent | none | none |
| Gelatin plate | not liq-efied | not liq-efied | not liq-efied | not liq-efied | not liq-efied | not liq-efied | not liq-efied | not liq-efied |
| Desoxycholate medium |  |  |  |  |  |  |  |  |
| growth | + | + | + | + | + | + | + | + |
| Growth at 38° C | − | − | + | − | − | ++ | ± | ++ |
| Growth at 37° C | + | + | ++ | + | + | ++ | + | ++ |
| Growth at 42° C | − | − | + | − | − | ++ | ± | ± |
| Litmus milk |  |  |  |  |  |  |  |  |
| reduction | − | − | − | − | − | − | − | − |
| liquefaction | − | − | − | − | − | − | − | − |
| BCP milk |  |  |  |  |  |  |  |  |
| pH | alkaline | alkaline | alkaline | alkaline | alkaline | alkaline | alkaline | alkaline |
| liquefaction | − | − | − | − | − | − | +++ | − |
| Assimilation of p-hydroxybenzoic acid | + | + | + | + | − | ++ | + | ± |
| Reduction of nitrate | ++ | +++ | +++ | +++ | +++ | +++ | ++ | ++ |
| Utilization of citric acid |  |  |  |  |  |  |  |  |
| Koser's medium | ++ | ++ | ++ | ++ | ++ | ++ | ++ | ++ |
| Christensen's medium | +++ | +++ | +++ | +++ | +++ | +++ | +++ | +++ |
| Hydrolysis of starch | − | − | − | − | − | − | − | − |

The identification experiments mentioned above were carried out according to "Manual of Microbiological Methods", M. J. Pelczar Jr. McGrow Hill (1957). Cultivation was carried out at 30° C.

Identification was made according to "Bergey's Manual of Determinative Bacteriology, 7th Ed. (1957).

I. AJ 3854

This strain is oxidase-positive, gram-negative, and rods, and has polar flagella, and therefore, belongs to the genus Pseudomonas. This strain resembles Ps. riboflavina, Ps. denitrificans and Ps. indoloxydans in the points that this strain does not form water-soluble pigments, does not liquefy gelatine, and grows at 25° C but does not grow at 37° C.

However, this strain is different from Ps. riboflavina since Ps. riboflavina decomposes riboflavine, and does not utilize ammonia and nitrates. This strain is different from Ps. denitrificans since it does not show denitrofication from nitrates. This strain is also different from Ps. indoloxydans since it does not form indigotin from indole.

Therefore, this strain is a novel species of the genus Pseudomonas, and designated as *Pseudomonas thiazolinophilum*.

This strain has been deposited with Fermentation Research Institute, Agency of Industrial Science and Technology, at Inage, Chiba Ciy, Japan, in the accession number of FERM-P 2810.

II. AJ 3863, AJ 3864, AJ 3865, AJ 3866 and AJ 3867

These strains are identified with *Pseudomonas ovalis*, and have been deposited with the Fermentation Research Institute with the accession numbers of FERM-P 2811 (AJ 3863), FERM-P 2812 (AJ 3864), FERM-P 2813 (AJ 3865), FERM-P 2814 (AJ 3866) and FERM-P 2815 (AJ 3867).

III. AJ 3868, AJ 3869, AJ 3870, AJ 3871, AJ 3872 and AJ 3873

These strains are identified with *Pseudomonas desmolytica*, and deposited with the Fermentation Research Institute in the accession numbers of FERM-P 2816 (AJ 3868), FERM-P 2817 (AJ 3869), FERM-P 2818 (AJ 3870), FERM-P2819 (AJ 3871), FERM-P 2820 (AJ 3872), and FERM-P 2821 (AJ 3873).

IV. AJ 3874

This strain is identified with Pseudomonas cohaerens, and deposited with the Fermentation Research Institute with the accession number of FERM-P 2831.

In order to produce ATC hydrolyzing enzyme, the microorganisms mentioned above are cultured in conventional medium of a pH 6 to 9, which contains carbon sources, nitrogen sources, inorganic ions, and when required, minor organic nutrients.

Carbon sources are conventional ones such as glucose, sucrose, glycerine, ethanol, and acetic acid. suitable Nitrogen sources are, for example, ammonium ions, and gaseous ammonia. Minor organic nutrients are, for example, vitamins and amino acids, and crude materials containing those minor organic nutrients such as yeast extract, peptone, bouillon, and corn steep liquor.

Inorganic ions are conventional ones such as manganese ions, ferric ions, ferrous ions, phosphate ions, potassium ions and magnesium ions. Manganese ions and ferrous ions are preferably used in an amount more than 0.01 mM, and more preferably 0.1 mM.

Cultivation is carried out under aerobic conditions at 20° to 40° C for 1 to 3 days.

High enzyme activity is possessed by the resulting culture broth and especially in microbial cells. And as the enzyme source, culture broth, intact cells, homogenate of cells, sonicate of cells, freeze-dried cells, cells dried with solvent and so on are preferably used. Protein fractions separated from, for example, the homogenate of the cells or sonicate of the cells by conventional methods such as gel-filtration or salting-out method are also used as a preferably enzyme source.

Especially, perferably are cells which have been contacted with an organic solvent or a surfactant, homogenate of cells, sonicate of cells, and cells treated with lytic enzymes of microbial cells are preferably used.

The preferred organic solvents are lower alkanols such as methanol and ethanol, aromatic hydrocarbons such as toluene and xylene, alkylketones such as acetone and methylethyl-ketone and chlorinated alkanes such as chloroform. Usually the cells are suspended in the organic solvent or an aqueous solution of the organic solvent for 10 to 120 minutes at 20° to 60° C.

Surfactants are preferably cationic or anionic ones such as salts of higher fatty acids, sulfonic acid alkyl esters, alkylbenzene sulfonates, salts of bile acid, alkylamines, and quaternary ammonium salts. Cells are suspended and contacted in the surfactant solution containing 0.0005 to 0.1% of the surfactant.

Homogenate of cells and sonicate of cells can be prepared in conventional and well-known manner.

Lytic enzyme of microbial cells is produced by various microorganisms such as bacterium, and actinomycetes.

The aqueous reaction mixture contains the enzyme or the enzyme source as mentioned above, ATC, and when required, pyridoxalphosphate and/or metal ions.

When the reaction mixture also contains 0.03 to 2 mM ferrous ions or 0.03 to 2mM ferric ions, higher yield of L-cysteine and L-cystine is obtained. Hydroxylamine or semicarbazide prevents decomposition of L-cysteine or L-cystine accumulated in the reaction mixture.

The amounts of ATC in the reaction mixture are preferably 0.1 to 30% and more preferably 0.5 to 10%. During the reaction, therefore pH of the reaction mixture is maintained at 5 to 11, and preferably 7 to 9.5. The reaction temperature is preferably maintained at 15° to 60° C, and more preferably at 30° to 50° C.

Usually both L-cysteine and L-cystine are accumulated in the reaction mixture. However, it is possible to produce exclusively L-cystine by carrying out the reaction under oxidative conditions, on the other hand, higher amounts of L-cysteine are produced under reducing conditions.

Usually, since L-cystine is moe insoluble than L-cysteine, L-cysteine in the reaction mixture is oxidized to L-cystine, and L-cystine is crystallized from the reaction mixture. L-Cystine is easily converted to L-cysteine by electrolytic reduction.

L-Cysteine and L-cystine in the reaction mixture were determined by liquid chromatography and bio-assay method using *Leuconostoc citrovorum* ATCC 8081. This strain responds to both L-cysteine and L-cystine, and does not respond to D-cysteine and D-cystine. Therefore, when L-cysteine and L-cystine is determined by the bio-assay method, total amount of L-cysteine and L-cystine is obtained. This total amount is shown in this specification as L-cystine.

EXAMPLE 1

Soil was spread on the following screening medium, and the medium was incubated at 30° C for 4 days:

| Screening medium: | | |
|---|---|---|
| DL-ATC . 3H$_2$O | 0.3 | g/dl |
| glycerol | 1.0 | g/dl |
| yeast extract | 0.01 | g/dl |
| KH$_2$PO$_4$ | 0.1 | g/dl |
| MgSO$_4$ . 7H$_2$O | 0.05 | g/dl |
| agar | 2.0 | g/dl |
| pH 7 (NaOH) | | |

Strains grown on the screening medium were separated and inoculated in the following culture medium, and cultured at 30° C for 24 hours:

| Culture medium: | | |
|---|---|---|
| glycerol | 1.0 | g/dl |
| yeast extract | 0.5 | g/dl |
| peptone | 0.5 | g/dl |
| bouillon | 0.5 | g/dl |
| NaCl | 0.5 | g/dl |
| DL-ATC . 3H$_2$O | 0.2 | g/dl |
| pH 7.0 (KOH) | | |

Cells grown on the culture medium were collected and suspended in an aqueous reaction mixture containing, per deciliter, 1.0 g DL-ATC·3H$_2$O, and 1.0 g KH$_2$PO$_4$, of pH 8, and the suspension was held at 30° C for 24 hours. L-Cysteine and L-cystine in the culture medium were determined.

Most effective L-cystine producers, AJ 3854, AJ 3863, AJ 3864, AJ 3865, AJ 3866, AJ 3867, AJ 3868, AJ 3869, AJ 3870, AJ 3871, AJ 3872, AJ 3873 and AJ 3874 were selected as mentioned above.

EXAMPLE 2

Cells of *Pseudomonas thiazolinophilum* AJ 3854 (FERM-P 2810) grown on a medium containing per deciliter, 1 g glycerol, 0.5 g yeast extract, 0.5 g peptone, 0.5 g bouillon, 0.5 g NaCl and 2 g agar, of pH 7.0, at 30° C for 24 hours were collected and inoculated in an aqueous culture medium containing, per deciliter, 2 g glucose, 0.3 g (NH$_4$)$_2$SO$_4$, 0.2 g DL-ATC·3H$_2$O, 0.1 g KH$_2$PO$_4$, 0.05 g MgSO$_4$·7H$_2$O, 2 g CaCO$_3$, 1 mg FeSO$_4$·7H$_2$O, 0.8 mg MnSO$_4$·4H$_2$O, and the amount of MnSO$_4$·4H$_2$O shown in Table 1. Fifty ml of the culture medium placed in 500 ml flasks were held at 30° C for 24 hours with shaking.

One volume of the culture medium at each cultivation time listed in Table 1 is mixed to one volume of ATC solution containing, per deciliter, 2 g DL-ATC·3H$_2$O, 2 g KH$_2$PO$_4$ and 0.28 g NH$_2$OH·HCl and of pH 8.2 and the mixture was held at 40° C for 2 hours. Total amount of L-cysteine and L-cystine was determined by the bio-assay method.

Growth of the microorganism in the aqueous culture medium was determined by measuring optical density at 562 nm of the culture broth diluted to 26 times with 0.1 N HCl (O.D.).

The results are shown in Table 1.

DL-ATC·3H$_2$O, of pH 7.0. Cells were collected by centrifuging, and washed with 0.8% NaCl.

A reaction mixture (5ml) containing 1 g DL-ATC·3H$_2$O, 1 g KH$_2$PO$_4$ and 5 g the washed cells was held at 40° C for 2 hours.

Table 1

| MnSO$_4$ . 4H$_2$O added | | Cultivation time (hr) | | | | | | | | |
|---|---|---|---|---|---|---|---|---|---|---|
| | | 0 | 3 | 6 | 9 | 12 | 15 | 18 | 21 | 24 |
| — | growth | 0.005 | 0.025 | 0.143 | 0.468 | 0.74 | 0.75 | 0.74 | 0.72 | 0.71 |
| | L-cystine µg/ml/O.D. | — | 1140 | 2620 | 1860 | 1060 | 1100 | 1000 | 853 | 1090 |
| 10 mM | growth | 0.006 | −0.019 | 0.094 | 0.312 | 0.62 | 0.75 | 0.73 | 0.73 | 0.71 |
| | L-cystine µg/ml/O.D. | — | 526 | 21800 | 3890 | 2160 | 1810 | 1870 | 1280 | 1280 |

In the medium containing 10mM MnSO$_4$·4H$_2$O, Ps. desmolytica AJ 3871 was cultured for 6 hours.

In the 100 ml broth thus obtained, 3 g DL-ATC·3H$_2$O, and 0.14 g NH$_2$OH·HCl were added and maintained for 20 hours, then 2.3 g L-cystine was formed.

EXAMPLE 3

Ps. thiazolinophilum AJ 3854 was cultured at 30° C for 6 hours in the medium shown in Example 2, except that in place of 10 mM, of the same manganese salt the amount of MnSO$_4$·4H$_2$O shown in Table 2 were contained.

Using each culture broth thus obtained, the amount of L-cystine shown in Table 2 was formed in the analogous reaction mixture to that shown in Example 2, after holding the reaction mixture at 40° C for 2 hours.

Table 2

| MnSO$_4$ . 4H$_2$O | | L-cystine formed | |
|---|---|---|---|
| 0 | | 446 | µg/ml (100) |
| 0.1 | mM | 1214 | (272) |
| 0.5 | | 1386 | (311) |
| 1 | | 1444 | (324) |
| 5 | | 1480 | (332) |
| 10 | | 1472 | (330) |

EXAMPLE 4

Pseudomonas thiazolinophilum AJ 3854 (FERM-P 2810) was cultured at 30° C for 15 hours in an aqueous medium, of which 50 ml batches were placed in 500 ml flasks, and which contains, per deciliter, 2 g glycerol, 0.5 g yeast extract, 0.5 g peptone, 0.25 g NaCl, 0.2 g Precipitates formed in the reaction mixture were dissolved by adding 6N HCl to the reaction mixture, and the amount of L-cystine in the reaction mixture was determined by the bio-assay method.

On the other hand, the washed cells were suspended in a surfactant solution each containing amount shown in Table 3 of dodecylsulfate sodium salt or cethyltrimethylammonium chloride. The suspension was held at 30° C for one hour.

The cells were suspended in the same reaction mixture mentioned above and the suspension was held at 40° C for 2 hours.

The results are shown in Table 3.

Table 3

| Surfactant | | L-cystine formed µg/ml | Relative activity % |
|---|---|---|---|
| Dodecylsulfate sodium salt | 0.005% | 2420 | 110 |
| | 0.01 | 3600 | 162 |
| | 0.05 | 3370 | 152 |
| | 0.1 | 33 | 1 |
| | 0.5 | 0 | 0 |
| Cethyltrimethyl-ammoniumchloride | 0.01 | 2320 | 104 |
| | 0.05 | 2990 | 135 |
| | 0.1 | 156 | 7 |
| | 0.5 | 30 | 1 |
| | 1 | 14 | 1 |
| none | — | 2220 | 100 |

EXAMPLE 5

Pseudomonas thiazolinophilum AJ 3854 was cultured in the same medium as in Example 4 at 30° C for 24 hours. The cells were collected by centrifuging and washed with 0.8% NaCl.

The cells were suspended in the same reaction mixture as in Example 4 and the suspension was held at 30° C for 2 hours.

On the other hand, the washed cells prepared by the same manner as mentioned above was subjected to super sonic waves with Model UR-200P (Tomy-Seiko Co., Ltd.) for the time shown in Table 4.

The sonicate was used in place of the washed cells in the analogous reaction mentioned above.

L-Cystine formed in each reaction mixture was determined by the bio-assay method. Optical density of the reaction mixture diluted to 26 times was also determined at 562 nm.

The results are shown in Table 4.

Table 4

| Subjected time to super sonic waves | O.D. | L-cystine formed |
|---|---|---|
| 0 min. | 1.20 | 590 µg/ml |
| 1 | 0.78 | 700 |
| 2 | 0.372 | 910 |
| 3 | 0.318 | 950 |
| 4 | 0.285 | 630 |

EXAMPLE 6

Pseudomonas ovalis AJ 3865 (FERM-P 2813) was cultured in the analogous manner to that in Example 4. Ten ml of the resultant culture broth was added with 0.5 ml of toluene, held at 30° C for 30 minutes, and further added with 10 ml of a solution containing 2 g/dl DL-ATC·3H$_2$O, 1 g/dl KH$_2$PO$_4$ and 0.14 g/dl NH$_2$OH·HCl.

The mixture was adjusted to pH 8.2, held at 40° C for 2 hours.

The reaction mixture of toluene treated cells contained 1,100 µg/ml L-cystine, while the reaction mixture of intact cells contained 310 µg/ml L-cystine.

EXAMPLE 7

Cells of Pseudomonas desmolytica AJ 3891 (FERM-P 2819) prepared in the same manner as in Example 5 were treated with 5% chloroform as the analogous manner in Example 6.

In the case of cells treated with chloroform, 350 µg/ml of L-cystine was formed, while in the case of intact cells, 240 µg/ml of L-cystine was formed.

EXAMPLE 8

Pseudomonas thiazolinophilum AJ 3854 was cultured in the same manner as in Example 5.

On the other hand, Bacillus subtilis YT-25 which is capable of producing lytic enzyme of cells was cultured at 30° C for 30 hours, in a medium containing, per deciliter, 1 g peptone and 1 g bouillon, 0.3 g NaCl and 0.5 g glucose, of pH 6.0, as shown in Agr. Biol. Chem. 38, 2305 (1974).

The culture broth of AJ 3895 (9 ml) was mixed with 1 ml of the culture broth of YT-25 or with 1 ml of water. Each mixture was held at 30° C for 1 hour.

Thereafter these mixtues were both added, per deciliter, with 1 g DL-ATC·3H$_2$O and 1 g KH$_2$PO$_4$, and held for 2 hours at 40° C.

In the former, 390 µg/ml L-cystine was produced, while, in the latter, 290 µg/ml L-cystine was produced.

EXAMPLE 9

Washed cells of Pseudomonas thiazolinophilum AJ 3854 were prepared.

A reaction mixture containing, per deciliter, 5 g the washed cells, 1 g DL-ATC·3H$_2$O, 0.14 g NH$_2$OH·HCl and 1 g KH$_2$PO$_4$, of pH 8 was held at 40° C. The amounts of L-cysteine and L-cystine at each time shown in Table 5 were determined by the bio-assay method and liquid chromatography.

The results are shown in Table 5.

Table 5

|  | Reaction time (hr) | | | |
|---|---|---|---|---|
|  | 1 | 7 | 24 | 48 |
| L-cysteine | 2.48 | 2.51 | 1.83 | 0.63 |
| L-cystine | 1.22 | 1.89 | 3.79 | 4.96 |

EXAMPLE 10

An aqueous culture medium was prepared containing, per deciliter, 1 g glycerol, 0.5 g yeast extract, 0.5 g peptone, 0.5 g bouillon, 0.5 NaCl, and 0.2 g DL-ATC·3H$_2$O, adjusted to pH 7. Fifty ml batches of the aqueous culture medium were placed in 500 flasks, inoculated with each microorganism shown in Table 6, and held at 30° C for 16 hours with shaking.

Cells in the culture broth were collected by centrifuging, and freeze-dried.

The freeze-dried cells (3 g/dl) were suspended in 1 liter of an aqueous solution containing 1 g/dl DL-ATC·3H$_2$O, 1 g/dl KH$_2$PO$_4$, and 0.14 g/dl NH$_2$OH·HCl, and of pH 8, and the reaction mixture was held at 30° C for 53 hours.

Subsequently, the reaction mixture was added with 6 N NaOH to dissolve the precipitates formed. The amount of L-cystine in the supernatant of the reaction mixture was determined by the bio-assay method.

Table 6

| Microorganism | | L-Cystine formed µg/ml |
|---|---|---|
| Achromobacter delmarvae | FERM-P 21 | 237 |
| Alcalgenes denitrificans | ATCC 15173 | 50 |
| Bacillus brevis | ATCC 8185 | 43 |
| Brevibacterium flavum | ATCC 13826 | 22 |
| Enterobacter aerogenes | FERM-P 2764 | 184 |
| Enterobacter aerogenes | IAM 1183 | 173 |
| Ervinia carotovora | FERM-P 2766 | 24 |
| Escherichia coli | FERM-P 2763 | 10 |
| Micrococcus sodonensis | ATCC 11880 | 206 |
| Mycoplana dimorpha | ATCC 4279 | 146 |
| Serratia marcescens | FERM-P 2765 | 28 |
| Flavobacterium acidoficum | ATCC 8366 | 10 |
| Pseudomonas ovalis | FERM-P 2762 | 68 |
| Sarcina lutea | ATCC 272 | 5100 |

Isolation of L-cystine crystal was carried out from the culture broth of Sarcina lutea ATCC 272 as follows; supernatant of reaction mixture was obtained by centrifugation, 5 g active carbon was added and heated. After filtration 990 ml filtrate was aerated for overnight, and concentrated. The crystal formed was filtered, washed with water, and dried. The final molar yield was 63% (3.8 g).

EXAMPLE 11

Each microorganism listed in Table 7 was cultured at 30° C, for 24 hours on the agar medium consisted of 1 g/dl glycerol, 0.5 g/dl yeast extract, 0.5 g/dl peptone, 0.5 g/dl meat extract, 0.5 g/dl NaCl, and 0.2 g/dl DL-ATC·3H$_2$O (pH 7.0) and 2 g/dl agar. About 250 mg of wet cells were suspended in 5 ml of reaction mixture containing 1 g/dl DL-ATC·3H$_2$O, 1 g/dl KH$_2$PO$_4$, 0.14 g/dl NH$_2$OH·HCl (pH 8.0), and maintained at 30° C, for 24 hours. The amount of L-cystine shown in Table 7 was formed in the reaction mixture.

Table 7

| | | L-cystine formed mg/ml |
|---|---|---|
| Ps. ovalis | AJ 2236 | 0.068 |

Table 7-continued

| | | L-cystine formed mg/ml |
|---|---|---|
| Ps. ovalis | AJ 3863 | 3.945 |
| Ps. ovalis | AJ 3864 | 2.345 |
| Ps. ovalis | AJ 3865 | 6.145 |
| Ps. ovalis | AJ 3866 | 4.050 |
| Ps. ovalis | AJ 3867 | 5.690 |
| Ps. desmolytica | AJ 3868 | 3.631 |
| Ps. desmolytica | AJ 3869 | 6.050 |
| Ps. desmolytica | AJ 3870 | 5.445 |
| Ps. desmolytica | AJ 3871 | 6.240 |
| Ps. desmolytica | AJ 3872 | 0.720 |
| Ps. desmolytica | AJ 3873 | 0.930 |
| Ps. cohaerens | AJ 3874 | 4.737 |
| Ps. thiazolinophilum | AJ 3854 | 6.050 |

EXAMPLE 12

Ps. thiazolinophilum AJ 3854 was cultured aerobically at 30° C for 14 hours in the medium containing 2 g/dl glucose, 0.5 g/dl yeast extract, 0.5 g/dl peptone, 0.25 g/dl NaCl, 0.1 g/dl $KH_2PO_4$, 0.05 g/dl $MgSo_4\cdot 7H_2O$, 0.2 g/dl $DL\text{-}ATC\cdot 3H_2O$ (pH 7). Cells harvested from 100 ml broth were resuspended in the reaction mixture described in Example 11, and maintained at 30° C for 20 hours. L-Cystine formed was 0.595 g (molar yield 98%).

Active carbon (0.1 g) was added in the supernatant of the reaction mixture, heated, filtrated, and adjusted the pH to 7. After overnight aeration, 0.488 g of L-cystine was obtained (final yield 80%).

EXAMPLE 13

Three gram cells of Ps. thiazolinophilum AJ 3854 obtained in Example 12 were suspended in 50 ml of 0.1 M $K\text{-}PO_4$ buffer, and sonicated at 20 KC for 5 minutes. Into the supernatant of sonicate, 0.5 g $DL\text{-}ATC\cdot 3H_2O$ and 0.07 g $NH_2OH\cdot HCl$ were added, and adjusted the pH at 8. After 24 hours reaction at 30° C, 6.1 mg/ml L-cystine was formed.

EXAMPLE 14

Cells of Ps. thiazolinophilum AJ 3854 were obtained and enzyme reaction was carried out by the same method as described in Example 12 except the addition of 0.02% sodium dodecyl sulfate. In 5 hours DL-ATC was all diminished and 6.05 mg/ml L-cystine was formed (molar yield 99%).

EXAMPLE 15

In 100 ml broth of Ps. ovalis AJ 3865 obtained by the same method as Example 12, 50 mg cetyltrimethyl ammonium chloride, 1 g $DL\text{-}ATC\cdot 3H_2O$ and 0.14 g $NH_2OH\cdot HCl$ were added.

In 7 hours incubation at 30° C, 0.59 g L-cystine was formed (molar yield 97%).

EXAMPLE 16

The wet cells of Ps. desmolytica AJ 3871 obtained by the same method as described in Example 12 produced 1890 μg/ml/hr L-cystine. The cell concentration used was 5%. In comparison, lyophilized cells produced 2750 μg/ml/hr L-cystine.

EXAMPLE 17

Cells of Ps. thiazolinophilum AJ 3854 obtained in the analogous manner to that in Example 12 (wet weight being 1 g) were suspended in 4 ml of water, and chilled. To this suspension was added with 45 mg methylene-bis-acrylamide which is, introduced $N_2$ gas, then 3.5 mg ammonium persulfate and 8 μl N,N'-dimethylaminopropionitrile were added. After cooling for 1 hour, the gels formed were filtered with 50 mesh wire gauze, and washed with 0.8% NaCl solution. One gram of the gels was suspended in 2 ml of the reaction mixture shown in Example 12. The reaction mixture was held at 30° C for 24 hours, and 5.40 mg/ml L-cystine were found in the reaction mixture by the bio-assay method.

EXAMPLE 18

Ps. thiazolinophilum AJ 3854 was cultured in the same medium as in Example 4 at 30° C for 24 hours, and the cells were collected by centrifuging.

To the reaction mixture shown in Example 4 there was added the amount of the compound listed in Table 8.

The reaction was carried out at 30° C for 7 hours, and contained the amount of L-cystine as shown in Table 8.

Table 8

| Compound added | | L-cystine formed (g/dl) |
|---|---|---|
| $NH_2OH\cdot HCl$ | 0 mM | 0.14 |
| | 1 | 0.34 |
| | 5 | 0.55 |
| | 10 | 0.57 |
| | 20 | 0.61 |
| | 30 | 0.60 |
| | 50 | 0.57 |
| | 100 | 0.46 |
| $NH_2NHCONH_2$ | 0 | 0.17 |
| | 0.1 | 0.15 |
| | 1 | 0.19 |
| | 10 | 0.40 |
| | 100 | 0.33 |

What is claimed is:
1. A method for producing L-cysteine and/or L-cystine which comprises:
   a. holding 2-amino-thiazoline-4-carboxylic acid in an aqueous solution at a pH of 5 to 11 in the presence of an effective amount of enzyme produced by a microorganism; said enzyme being capable of converting 2-amino-thiazoline-4-carboxylic acid to L-cysteine and/or L-cystine, and said microorganism being capable of growing in a medium containing 2-amino-thiazoline-4-carboxylic acid as a nitrogen source, and of producing said enzyme; and
   b. recovering the L-cysteine and/or L-cystine formed from said aqueous solution.

2. The method of in claim 1, wherein said microorganism belongs to the genus Sarcina, Achromobacter, Alcaligenes, Bacillus, Brevibacterium, Enterobacter, Ervinia, Escherichia, Micrococcus, Mycoplana, Serratia, Flavobacterium, or Pseudomonas.

3. A method of claim 1, wherein said microorganism belongs to the species:
   Sarcina lutea
   Achromobacter delmarvae
   Alcaligenes denitrificans
   Bacillus brevis
   Brevibacterium flavum
   Enterobacter aerogenes
   Ervinia carotovora
   Escherichia coli
   Micrococcus sodonensis
   Mycoplana dimorpha Serratia marcescens
Pseudomonas thiazolinophilum
Pseudomonas ovalis
Pseudomonas desmolytica or
Pseudomonas cohaerens 4. A method of claim 1, wherein said microorganism is:

| | |
|---|---|
| Sarcina lutea | ATCC 272 |
| Achromobacter delmarvae | FERM-P 21 |
| Alcaligenes denitrificans | ATCC 15173 |
| Bacillus brevis | ATCC 8185 |
| Brevibacterium flavum | ATCC 13826 |
| Enterobacter aerogenes | FERM-P 2764 |
| Ervinia carotovora | FERM-P 2766 |
| Escherichia coli | FERM-P 2763 |
| Micrococcus sodonensis | ATCC 11880 |
| Mycoplana dimorpha | ATCC 4279 |
| Serratia marcescens | FERM-P 2765 |
| Pseudomonas thiazolinophilum | FERM-P 2810 |
| Pseudomonas ovalis | FERM-P 2762, FERM-P 2811, FERM-P 2812, FERM-P 2813, FERM-P 2814, or FERM-P 2815 |
| Pseudomonas desmolytica | FERM-P 2816, FERM-P 2817 FERM-P 2818, FERM-P 2819, FERM-P 2820 or FERM-P 2821 |
| or | |
| Pseudomonas cohaerens | FERM-P 2831. |

5. A method of claim 1, wherein said microorganism is capable of growing in a medium containing, per deciliter, 0.3 g 2-amino-thiazoline-4-carboxylic acid trihydrate, 1 g glycerol, 0.01 g yeast extract, 0.1 g $KH_2PO_4$, 0.05 g $MgSo_4 \cdot 7H_2O$, and 2 g agar.

6. A method of claim 1, wherein said enzyme is produced by culturing said microorganism in a medium containing 2-amino-thiazoline-4-carboxylic acid.

7. A method of claim 1, wherein said enzyme is produced by culturing in a medium containing manganese ions in an amount of more than 0.1 mM.

8. A method of claim 1, wherein said enzyme is produced by culturing in a medium containing ferrous ions in an amount of more than 0.1 mM.

9. The method of claim 1, wherein intact cells of said microorganism, a homogenate of the cells of said microorganism, freeze-dried cells of said microorganism, or a sonicate of the cells of said microorganism are used as the enzyme source.

10. The method of claim 1, wherein the cells of said microorganism which are used as the source of said enzyme have been contacted with an organic solvent.

11. The method of claim 10, wherein said organic solvent is a lower alkanol, an aromatic hydrocarbon, an alkylketone, or a chlorinated alkane.

12. The method of claim 1, wherein the cells of said microorganism which are used as the source of said enzyme have been contacted with a surfactant.

13. The method of claim 12, wherein said surfactant is a cationic surfactant or an anionic surfactant.

14. The method of claim 1, wherein the cells of said microorganism which are used as the source of said enzyme have been treated with a lytic enzyme of microbial cells.

15. A method of claim 1, wherein said aqueous solution contains hydroxylamine or semicarbazide.

16. A method of claim 1, wherein said aqueous solution contains ferrous ions in an amount of more than 0.036 mM.

17. A method of claim 1, wherein said aqueous solution contains ferric ions in an amount of more than 0.036 mM.

* * * * *